United States Patent
Yang et al.

(10) Patent No.: US 11,530,377 B2
(45) Date of Patent: Dec. 20, 2022

(54) BIOENVIRONMENTAL SIMULATION DEVICE AND METHOD

(71) Applicants: SEOUL NATIONAL UNIVERSITY R&DB FOUNDATION, Seoul (KR); SEOUL NATIONAL UNIVERSITY HOSPITAL, Seoul (KR)

(72) Inventors: Seung Hee Yang, Seoul (KR); Yon Su Kim, Seoul (KR); Dong Ki Kim, Seoul (KR); Sa Ram Lee, Gyeonggi-do (KR); Yong Chul Kim, Seoul (KR); Mi Yeon Yu, Seoul (KR); Ji Eun Kim, Seoul (KR)

(73) Assignees: SEOUL NATIONAL UNIVERSITY R&DB FOUNDATION, Seoul (KR); SEOUL NATIONAL UNIVERSITY HOSPITAL, Seoul (KR)

( * ) Notice: Subject to any disclaimer, the term of this patent is extended or adjusted under 35 U.S.C. 154(b) by 34 days.

(21) Appl. No.: 17/054,999

(22) PCT Filed: Dec. 10, 2019

(86) PCT No.: PCT/KR2019/017388
§ 371 (c)(1),
(2) Date: Nov. 12, 2020

(87) PCT Pub. No.: WO2020/122556
PCT Pub. Date: Jun. 18, 2020

(65) Prior Publication Data
US 2021/0214667 A1    Jul. 15, 2021

Related U.S. Application Data

(60) Provisional application No. 62/777,502, filed on Dec. 10, 2018.

(30) Foreign Application Priority Data

Dec. 10, 2019 (KR) .................... 10-2019-0163783

(51) Int. Cl.
*C12M 3/04* (2006.01)
*C12M 1/00* (2006.01)
*C12M 1/34* (2006.01)

(52) U.S. Cl.
CPC ............ *C12M 27/10* (2013.01); *C12M 23/22* (2013.01); *C12M 29/04* (2013.01); *C12M 29/14* (2013.01); *C12M 41/40* (2013.01); *C12M 41/42* (2013.01)

(58) Field of Classification Search
None
See application file for complete search history.

(56) References Cited

U.S. PATENT DOCUMENTS 4,435,168 A * 3/1984 Kennedy .............. B04B 5/0421
494/20
4,939,087 A    7/1990 Van Wie et al.
(Continued)

FOREIGN PATENT DOCUMENTS

| CN | 108728360 | * 11/2018 |
| JP | 2004-113222 A | 4/2004 |

(Continued)

OTHER PUBLICATIONS

Katkov and Mazur. "Factors Affecting Yield and Survival of Cells When Suspensions Are Subjected to Centrifugation". 1999. Cell Biochemistry and Biophysics. vol. 31, pp. 231-245. (Year: 1999).*
(Continued)

*Primary Examiner* — Donald R Spamer
*Assistant Examiner* — Nathan G Esperon
(74) *Attorney, Agent, or Firm* — The PL Law Group, PLLC (57) ABSTRACT

The bioenvironmental simulation device according to an embodiment of the present invention includes at least one
(Continued)

mounting unit on which cells to be measured are placed, a rotational force application unit configured to rotate the mounting unit so as to apply a rotational force to the cells to be measured placed on the mounting unit, and a culture liquid flow device through which a culture liquid flows across the mounting unit, wherein the culture liquid flows by the culture liquid flow device so as to apply a shear force to the cells to be measured.

17 Claims, 8 Drawing Sheets

(56) References Cited

U.S. PATENT DOCUMENTS

| | | | |
|---|---|---|---|
| 6,214,617 B1 | 4/2001 | Herman | |
| 9,500,642 B2 | 11/2016 | Blackman et al. | |
| 2010/0044309 A1* | 2/2010 | Lee | B01D 63/16 |
| | | | 210/636 |
| 2012/0083029 A1 | 4/2012 | Tsumura et al. | |
| 2014/0038279 A1* | 2/2014 | Ingber | C12M 35/04 |
| | | | 435/297.2 |
| 2014/0179505 A1* | 6/2014 | David | B04B 5/0421 |
| | | | 494/20 |
| 2015/0057141 A1* | 2/2015 | Toi | B04B 13/00 |
| | | | 494/10 |
| 2018/0259505 A1* | 9/2018 | Yang | C12M 35/04 |
| 2020/0333328 A1* | 10/2020 | Yang | C12M 27/10 |

FOREIGN PATENT DOCUMENTS

| | | | |
|---|---|---|---|
| JP | 2004113222 | * | 4/2004 |
| JP | 2015-073468 A | | 4/2015 |
| JP | 2017-136082 A | | 8/2017 |
| KR | 10-2010-0088297 A | | 8/2010 |
| KR | 10-2013-0120792 A | | 11/2013 |
| KR | 10-2018-0103692 A | | 9/2018 |

OTHER PUBLICATIONS

International Search Report for PCT/KR2019/017388 dated Apr. 2, 2020.

Office action dated Jun. 28, 2021 from Korean Patent Office in a counterpart Korean Patent Application No. 10-2019-0163783 (all the cited references are listed in this IDS.) (English translation is also submitted herewith.).

European Search Report For EP19894508.1 dated Oct. 11, 2022 from European patent office in a counterpart European patent application.

* cited by examiner

BIOENVIRONMENTAL SIMULATION DEVICE AND METHOD

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/017388, filed on Dec. 10, 2019, which claims priority to the benefit of U.S. Provisional Patent Application No. 62/777,502 filed on Dec. 10, 2018 and Korean Patent Application No. 10-2019-0163783 filed in the Korean Intellectual Property Office on Dec. 10, 2019, the entire contents of which are incorporated herein by reference.

TECHNICAL FIELD

The present invention relates to a bioenvironmental simulation device and a method thereof, and more specifically, to a bioenvironmental simulation device which provides a pressure through a rotational force and a shear force through a flow rate of a culture liquid to cells, and a method thereof.

BACKGROUND ART

Hypertension refers to a chronic disease in which a blood pressure is higher than the normal range. In general, for adults 18 years of age or older, when a person has a systolic blood pressure of 140 mmHg or higher, or a diastolic blood pressure of 90 mmHg or higher measured at rest, the person is diagnosed as having hypertension.

In most cases hypertension itself has no symptoms, but a person with hypertension may exhibit complications such as stroke, heart failure, retinopathy, coronary artery disease, renal failure, peripheral vascular disease and the like. In particular, it has been recently known that a reduction in the function of glomerulus and extensive fibrosis of kidney tissue may be caused by kidney damage due to the hypertension.

Cells inside a body of a hypertensive patient are subjected to a pressure applied higher than those of a normal person. Therefore, in order to study cells in a hypertensive environment, it is necessary to simulate a biological environment similar to that of the hypertensive patient by applying an artificial pressure to the cells.

For the simulation as described above, a method of chemically damaging cells is commonly used. However, such a method has a disadvantage that a cell damage may be caused by drugs. As another method, a method of simulating a hypertensive environment by directly applying a force to the cells has also been attempted. However, this also has low reproducibility, and since a device for implementing the above-described method has a complex structure and occupies a lot of installing space, there is a disadvantage that the related expenses are too high for practical use.

In addition, when applying a pressure to the cells without considering types of each individual cell, there is also a problem in that the hypertensive environment cannot be accurately simulated.

SUMMARY

An object of the present invention to provide a bioenvironmental simulation device which stably provides a constant pressure through a rotational force and a shearing force through a flow rate to cells so as to form an in vivo-like environment for simulation, and a method thereof.

To achieve the above object, according to an aspect of the present invention, there is provided a bioenvironmental simulation device including: at least one mounting unit on which cells to be measured are placed; a rotational force application part configured to rotate the mounting unit so as to apply a rotational force to the cells to be measured placed on the mounting unit; and a culture liquid flow device through which a culture liquid flows across the mounting unit, wherein the culture liquid flows by the culture liquid flow device so as to apply a shear force to the cells to be measured.

The at least one mounting unit may include: a first mounting part which has a first cell placing surface on which a first cell to be measured is placed on one surface of a separation membrane, and forms a first space through which a first culture liquid passes with facing the first cell placing surface; a second mounting part which has a second cell placing surface on which a second cell to be measured interacting with the first cell to be measured is placed on the other surface of the separation membrane, and forms a second space through which a second culture liquid passes with facing the second cell placing surface, wherein the second space is partitioned from the first space by the separation membrane.

The first and second culture liquids may be configured to pass through the first and second spaces at independent flow rates.

The culture liquid flow device may include: a first supply part configured to circulate the first culture liquid passing through the first space; and a second supply part configured to circulate the second culture liquid passing through the second space, wherein the second supply part is operated independently from the first supply part.

The first and second cell placing surfaces, on which the first and second cells to be measured are respectively disposed, may be subjected to: a pressure applied due to a resultant force of gravity and a rotational force generated by the rotational force application part in a first direction; and a shear force applied due to a flow of the first and second culture liquids by the culture liquid flow device in a second direction perpendicular to the first direction.

The second mounting part may be disposed outside of the first mounting part in the first direction.

The at least one mounting unit may include: a first inlet and a first outlet which are connected to the first mounting part and configured to allow the first culture liquid to inflow and outflow through the first space; and a second inlet and a second outlet which are connected to the second mounting part and configured to allow the second culture liquid to inflow and outflow through the second space, wherein the first inlet, the first outlet, the second inlet, and the second outlet are arranged in the second direction with respect to the first and second mounting parts, respectively.

The bioenvironmental simulation device may further include a pressure sensor disposed outside of the at least one mounting unit in the first direction to detect a pressure in the mounting unit.

The first and second mounting parts may include a transmissive member, of which one side faces the first and second spaces, and the other side is a transmissive surface exposed to an outside, which allows air to penetrate into the first and second spaces.

The transmissive member may include polydimethylsiloxane (PDMS).

The at least one mounting unit may include a plurality of mounting units radially disposed about the rotational force application part, and the bioenvironmental simulation device may further include: a unit mount configured to transmit a rotational force of the rotational force application part to the plurality of mounting units, and rotate together with the plurality of mounting units.

The unit mount may include: a plurality of mount legs which are radially divided and disposed, and the plurality of mounting units are respectively mounted thereon, such that an angle formed by the same with a ground is changed according to the rotational force of the rotational force application part.

The bioenvironmental simulation device may further include: an input unit configured to input a type of the cell to be measured; a database configured to store an appropriate rotational force and an appropriate shear force condition which are matched with the type of the cell to be measured; and a controller configured to control the rotational force application part and the culture liquid flow device so that a pressure and a shear force satisfying the appropriate pressure condition and the appropriate shear force condition are applied to the cells to be measured, based on the type of the cell to be measured, the appropriate pressure condition and the appropriate shear force condition which are matched with the type of the cell to be measured.

The appropriate pressure condition may include information on a relationship between a blood pressure of a body and the pressure applied to the cells to be measured under a condition in which the cells to be measured exist in the body, and the controller may calculate a value of an actual pressure which is the pressure applied to the cells to be measured under a condition in which the cells to be measured exist in the body having a blood pressure as much as a preset blood pressure value using the information in the appropriate pressure condition, and control the rotational force application part so that a pressure as much as the calculated value of the actual pressure is applied to the cells to be measured.

The appropriate shear force condition may include information on a relationship between a blood flow rate of a body and the shear force applied to the cells to be measured under a condition in which the cells to be measured exist in the body, and the controller may calculate a value of an actual shear force which is a shear force applied to the cells to be measured, under a condition in which the cells to be measured exist in the body having a blood flow rate as much as a predetermined blood flow rate using the information in the appropriate shear force condition, and control the culture liquid flow device so that a shear force as much as the calculated value of the actual shear force is applied to the cells to be measured.

The controller may calculate a speed of rotational motion of the mounting unit, which satisfies the appropriate pressure condition, to provide the calculated speed to the rotational force application part, and calculate a flow rate of the culture liquid, which satisfies the appropriate shear force condition, to provide the calculated flow rate to the culture liquid flow device.

The appropriate pressure condition and the appropriate shear force condition may be determined based on the pressure and the shear force within a range in which the cells to be measured can survive for a predetermined critical time in a predetermined critical probability or higher.

According to an embodiment of the present invention, it is possible to apply the desired pressure and shear force to cells to be tested by using a centrifugal force generated by rotation and flow of the fluids. By using the centrifugal force and shear force as described above, it is possible to stably apply the pressure to the cells without damaging the cells, while having advantages of providing high repeatability and reproducibility while also being easy to operate.

According to an embodiment of the present invention, by setting appropriate pressure and shear conditions for each type of the cells to be tested, it is possible to simulate an in vivo environment more closely to reality.

According to an embodiment of the present invention, by implementing a plurality of in vivo environments, it is possible to determine an interaction between the cells located in different environments from each other.

Through an embodiment of the present invention, it is possible to determine various operations and reactions of the cells inside the body of a patient according to the blood pressure thereof. Such achievements according to embodiments of the present invention may be applied to the development of drugs for treating hypertension and analysis of the effectiveness of the drugs, and may ultimately contribute to improve the health and quality of life of the hypertensive patients.

DETAILED DESCRIPTION

Configurations illustrated in the embodiments and drawings of the present disclosure are only preferred examples of the invention, and diverse modifications capable of replacing the embodiments and drawings of the present disclosure may be possible at a time of filing the present application.

Further, the same reference numerals or symbols in the drawings of the present disclosure will represent parts or components having substantially the same functions.

In addition, the terminology used herein is for the purpose of describing particular embodiments only and is not intended to limit the present invention thereto. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Further, the terms including numerals such as "first," "second," etc. in the present disclosure may be used to explain different components, but such components are not limited thereto. These terms are used only to distinguish one component from other components. For example, a first component may also be named a second component without departing from the scope of the present invention. Likewise, the second component may also be named the first component. The term "and/or" may include a coupling of a plurality of related items and/or any one among the plurality of related items.

In addition, the terms such as "part," "device," "block," "member," "module," and the like may refer to a unit to execute at least one function or operation. For example, the terms may refer to at least one hardware such as a field-programmable gate array (FPGA) or an application specific integrated circuit (ASIC), at least one operating process performed by at least one software stored in a memory or processor.

Hereinafter, embodiments according to the present invention will be described in detail with reference to the accompanying drawings.

Figure 1:
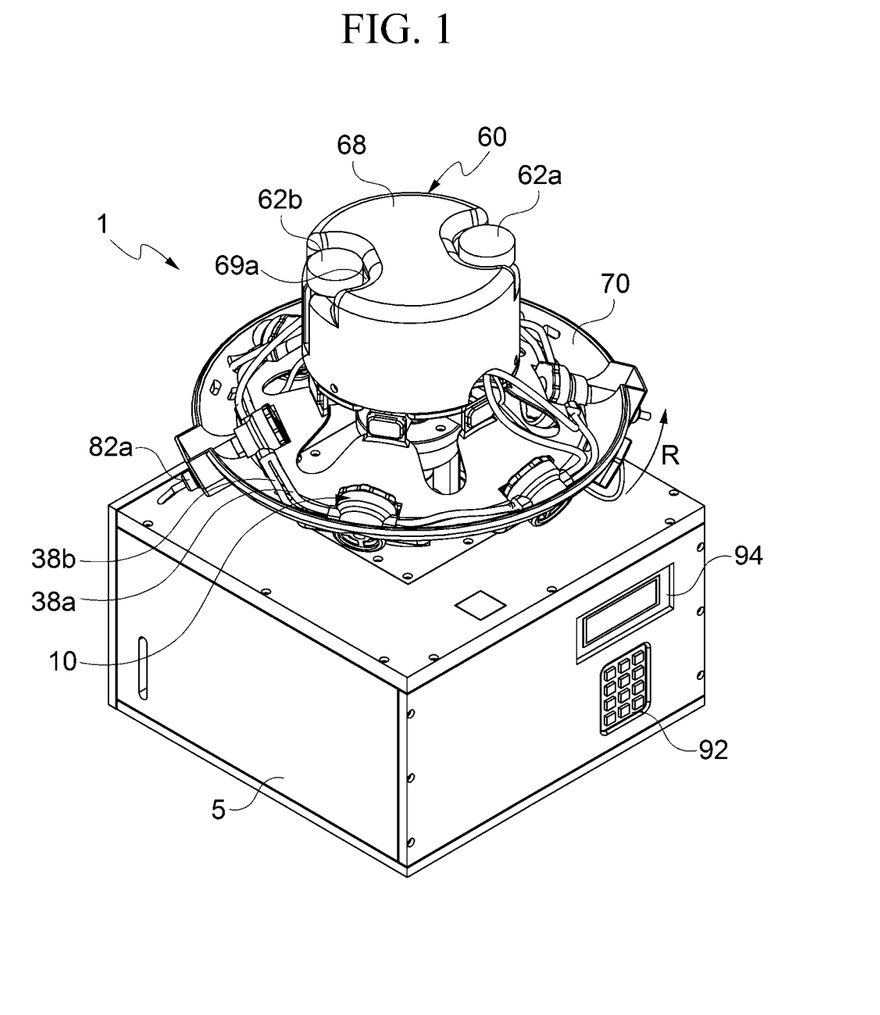
FIG. 1 is a perspective view of a bioenvironmental simulation device according to an embodiment of the present invention.
Figure 2:
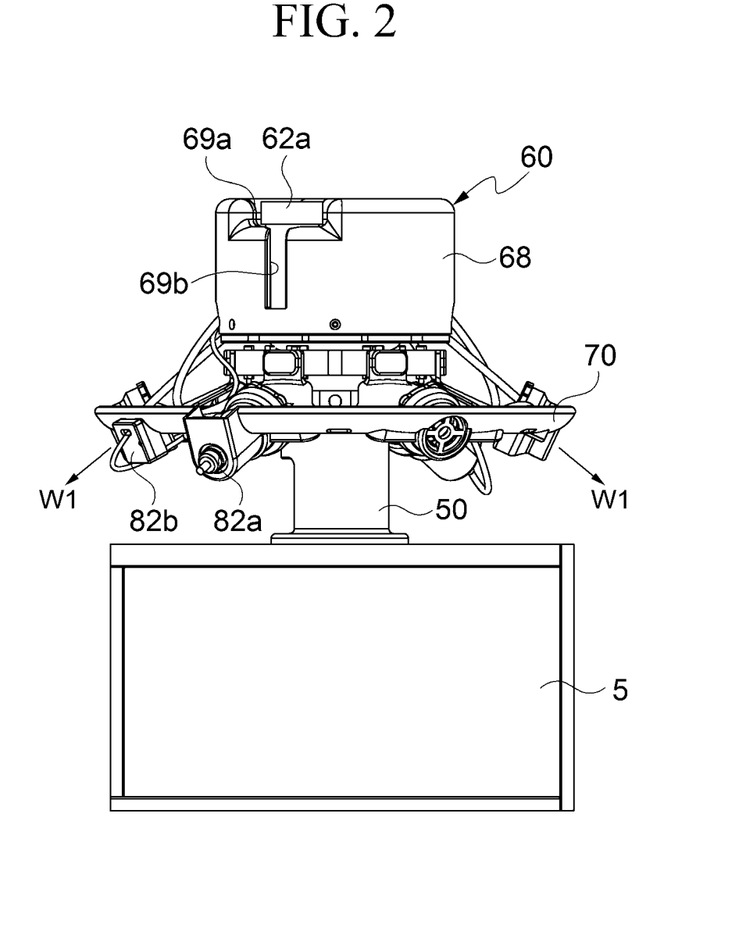
FIG. 2 is a side view of the bioenvironmental simulation device according to an embodiment of the present invention.
Figure 3:
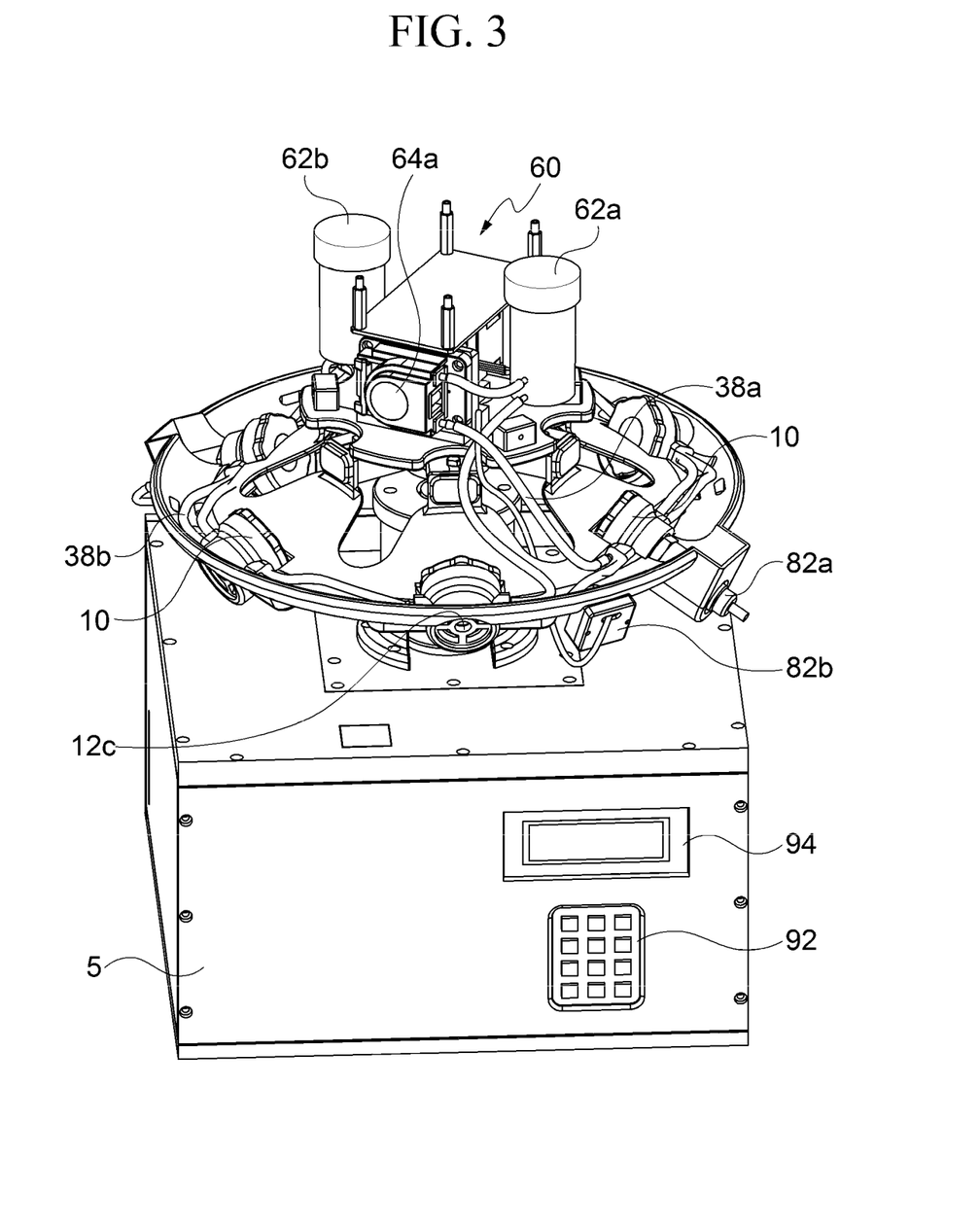
FIG. 3 is a perspective view illustrating a device cover removed from the bioenvironmental simulation device according to an embodiment of the present invention.

FIG. 1 is a perspective view of a bioenvironmental simulation device according to an embodiment of the present invention, FIG. 2 is a side view of the bioenvironmental simulation device according to an embodiment of the present invention, and FIG. 3 is a perspective view illustrating a device cover removed from the bioenvironmental simulation device according to an embodiment of the present invention.

A bioenvironmental simulation device 1 may determine various operations and reactions of cells by reproducing an environment similar to the in vivo environment.

The bioenvironmental simulation device 1 may include a mounting unit 10, a rotational force application part 50, and a culture liquid flow device 60.

Cells to be measured may be mounted in the mounting unit 10. The cells to be measured mounted in the mounting unit 10 may receive a pressure and a shear force through rotational motion and flow of a culture liquid to be described below. The mounting unit 10 includes a plurality of separated spaces capable of interacting with each other, and the plurality of spaces may be configured to allow different types of culture liquids or culture liquids with different flow rates to flow therein. At least one mounting unit 10 may be provided. In the present embodiment, the bioenvironmental simulation device 1 has six mounting units 10 which are arranged to be spaced apart from each other in a rotation direction about the rotational force application part 50, but the number thereof is not limited. The specific configuration of the mounting unit 10 will be described in detail below.

The rotational force application part 50 is provided to rotate the mounting unit 10. The rotational force application part 50 applies a centripetal force to the mounting unit 10, so as to allow the mounting unit 10 to perform a circular motion about a center point of the mounting unit 10 along a circular orbit as shown by an arrow R in FIG. 1. The plurality of mounting units 10 may be configured to perform the circular motion by the rotational force application part 50 with the same rotational center as each other. To this end, the rotational force application part 50 may include a power apparatus such as a general motor. The rotational force application part 50 rotates the mounting unit 10, such that a pressure may be applied to the cells to be measured in a first direction W1 (see FIG. 2), which is a resultant direction of gravity and rotational force.

The culture liquid flow device 60 is provided to flow the culture liquid to the mounting unit 10. The culture liquid flow device 60 may allow the culture liquid to flow across the mounting unit 10. The culture liquid flow device 60 can flow different types of culture liquids, or can flow culture liquids with different flow rates to the mounting unit 10. The culture liquid flow device 60 can flow the culture liquids to apply the shear force to the cells to be measured placed in the mounting unit 10.

The culture liquid flow device 60 may include first and second culture liquid storage parts 62a and 62b, a first supply part 64a (see FIG. 3), and a second supply part (not illustrated).

Each of the first and second culture liquid storage parts 62a and 62b may store culture liquids circulating to the mounting unit 10. The culture liquids stored in the first and second culture liquid storage parts 62a and 62b may be defined as first and second culture liquids, respectively. The first and second culture liquids may be different types of culture liquids, or may be the same culture liquid as necessary.

The first supply part 64a and the second supply part (not illustrated) are provided so that the first and second culture liquids stored in the first and second culture liquid storage parts 62a and 62b flow through the mounting unit 10. The first supply part 64a may be provided to be connected with the first culture liquid storage part 62a, and the second supply part may be provided to be connected with the second culture liquid storage part 62b. Although only the first supply part 64a is illustrated on one side in FIG. 3, but the second supply part (not illustrated) may be symmetrically disposed on the other side of the first supply part 64a. The first supply part 64a and the second supply part may include the power apparatus such as a pump. The first and second supply parts 64a may be independently operated by a controller. That is, the first supply part 64a and the second supply part (not illustrated) may be operated to circulate the first and second culture liquids stored in the first and second culture liquid storage parts 62a and 62b at independent flow rates, respectively.

The bioenvironmental simulation device 1 may include circulation tubes 38a and 38b. The circulation tubes 38a and 38b may include a first circulation tube 38a and a second circulation tube 38b. The first circulation tube 38a may be provided to connect the first culture liquid storage part 62a and the first supply part 64a with a first mounting part 30 to be described below among one or more mounting units 10. The second circulation tube 38b may be provided to connect the second culture liquid storage part 62b and the second supply part (not illustrated) with a second mounting part 40 to be described below among the one or more mounting units 10.

The culture liquid flow device 60 may include a device cover 68. The device cover 68 is provided to cover the first and second supply parts 64a so that the first and second supply parts 64a are not exposed to an outside, whereas the first and second culture liquid storage parts 62a and 62b are exposed to the outside. The device cover 68 may include concave portions 69a formed in a concave shape so that the first and second culture liquid storage parts 62a and 62b are located therein, and gauge check grooves 69b formed long in a longitudinal direction of the culture liquid storage part so as to indicate an amount of the culture liquids in the first and second culture liquid storage parts 62a and 62b.

The bioenvironmental simulation device 1 may include a unit mount 70.

The unit mount 70 may be provided so that at least one mounting unit 10 is mounted thereon. The unit mount 70 is provided so that at least one mounting unit 10 is mounted thereon to transmit the rotational force supplied from the rotational force application part 50 to the respective mounting units 10. The unit mount 70 may be formed in a shape of a rotating body. In the present embodiment, the unit mount 70 may have a shape of extending in a radial direction with respect to the rotational force application part 50 in consideration of the rotational force and gravity, with being inclined in a direction of gravity. However, the shape of the unit mount 70 is not limited thereto. The unit mount 70 may have any configuration so long as it can sufficiently connect the rotational force application part with the mounting unit 10 so as to transmit the rotational force of the rotational force application part 50 to the mounting unit 10. Further, in consideration of the resultant force of the rotational force of the unit mount 70 and gravity, as shown in FIG. 2, any configuration may be used so long as it can sufficiently support the mounting unit 10 with being inclined at an angle with respect to the ground. In the present embodiment, the configuration, in which a plurality of mounting units 10 are mounted on one unit mount 70, has been described as an example, but it is not limited thereto. For example, as will be described below, a plurality of divided unit mounts 70 may be radially disposed, and the respective mounting units 10 may be mounted on the plurality of radially disposed unit mounts 70.

The bioenvironmental simulation device 1 may include a hydraulic sensor (not illustrated), a pressure sensor 82a, and an acceleration sensor 82b.

The hydraulic sensor (not illustrated) is provided to detect a pressure due to the flow rate of the culture liquid flowing by the first and second supply parts of the culture liquid flow device 60. By adjusting the flow rate of the culture liquid, it is possible to control the shear force applied to the cells to be measured as described below.

The pressure sensor 82a and the acceleration sensor 82b are provided to detect the pressure and acceleration for the rotational force of the rotational force application part 50. The pressure sensor 82a may be mounted in the mounting unit 10 through a sensor mounting hole 12c (see FIGS. 3 and 6) formed in a lower portion of a unit body 12 to be described below.

Result values measured by the hydraulic sensor, the pressure sensor 82a, and the acceleration sensor 82b may be transmitted to a storage unit through wireless communication. The result values transmitted to the storage unit may be output to an output unit 94 or transmitted to a user terminal through wireless communication.

Figure 4:
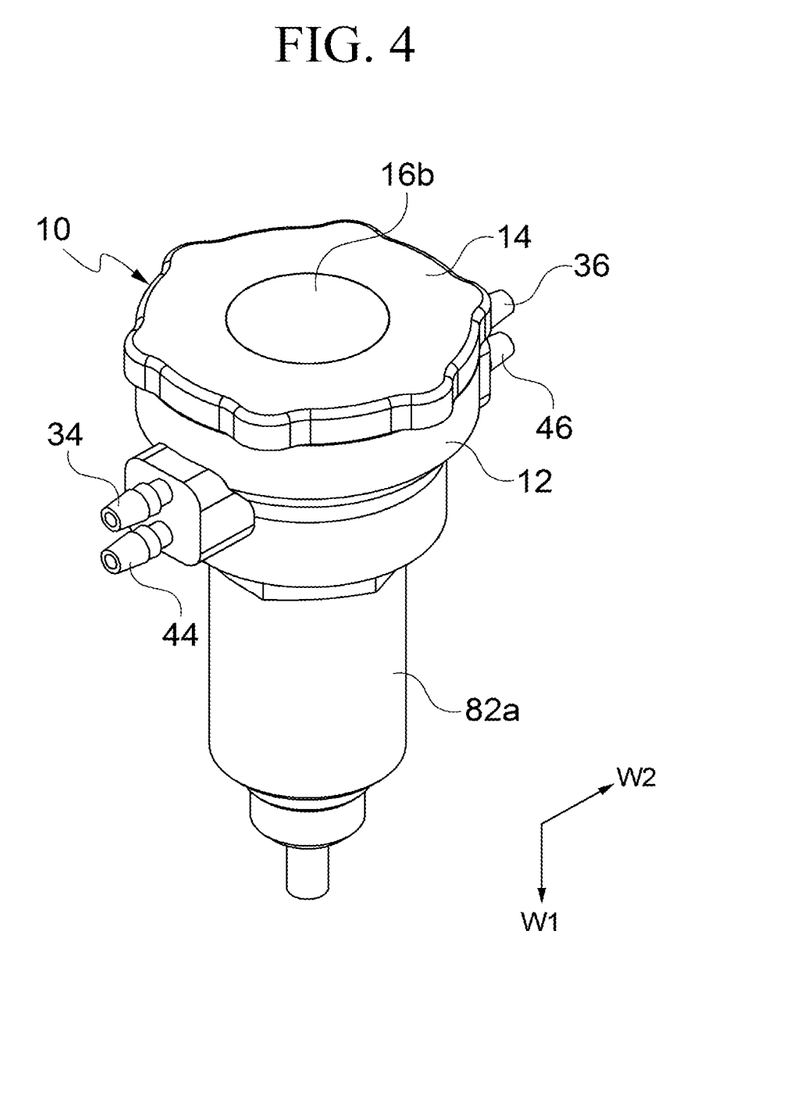
FIG. 4 is a perspective view of a mounting unit and a pressure sensor of the bioenvironmental simulation device according to an embodiment of the present invention.
Figure 5:
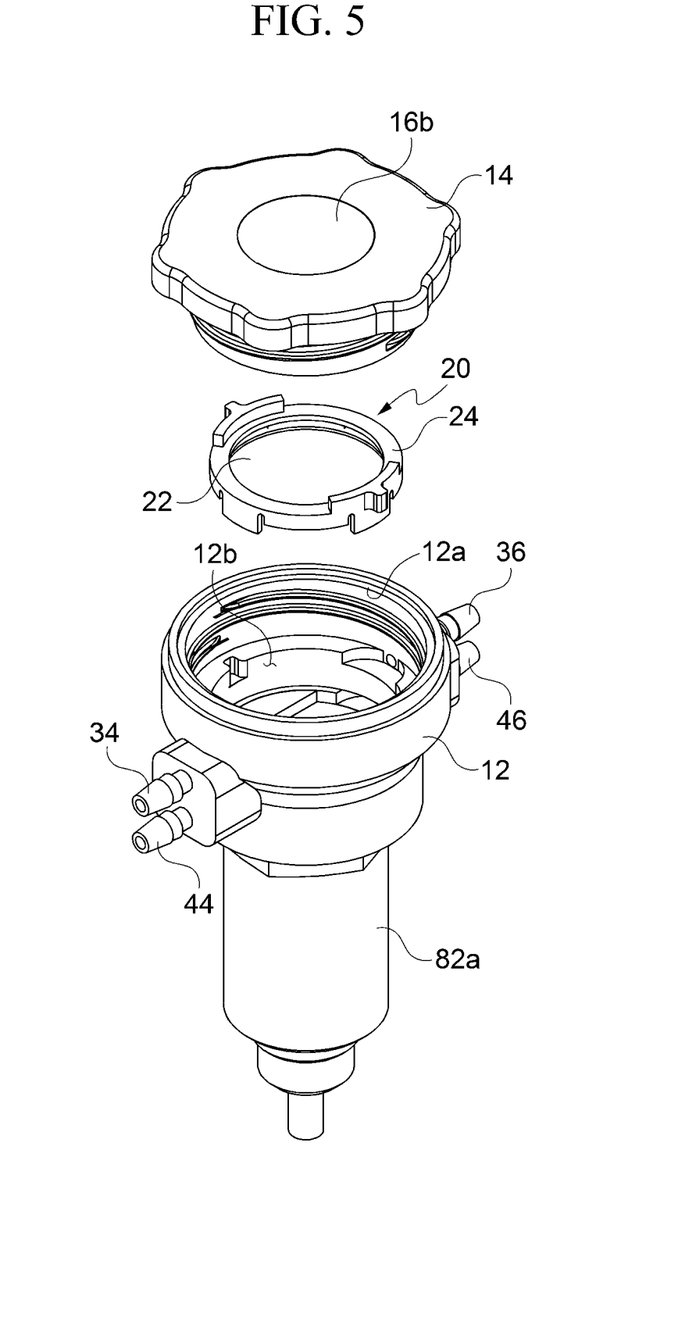
FIG. 5 is an exploded perspective view of the mounting unit and the pressure sensor of the bioenvironmental simulation device according to an embodiment of the present invention.
Figure 6:
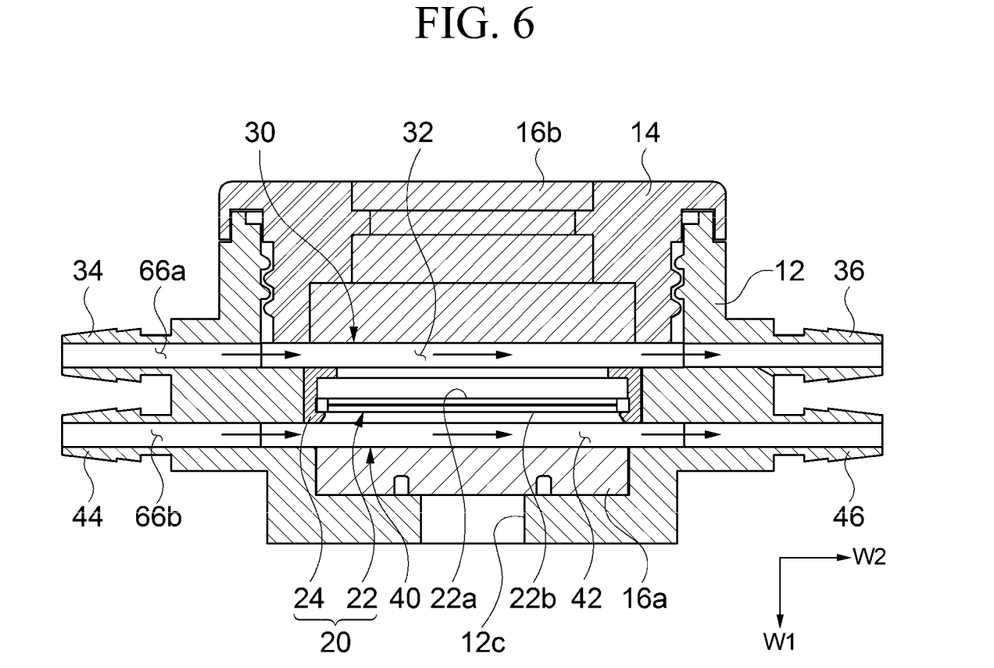
FIG. 6 is a cross-sectional view illustrating the mounting unit of the bioenvironmental simulation device according to an embodiment of the present invention and flow of a culture liquid.
Figure 7:
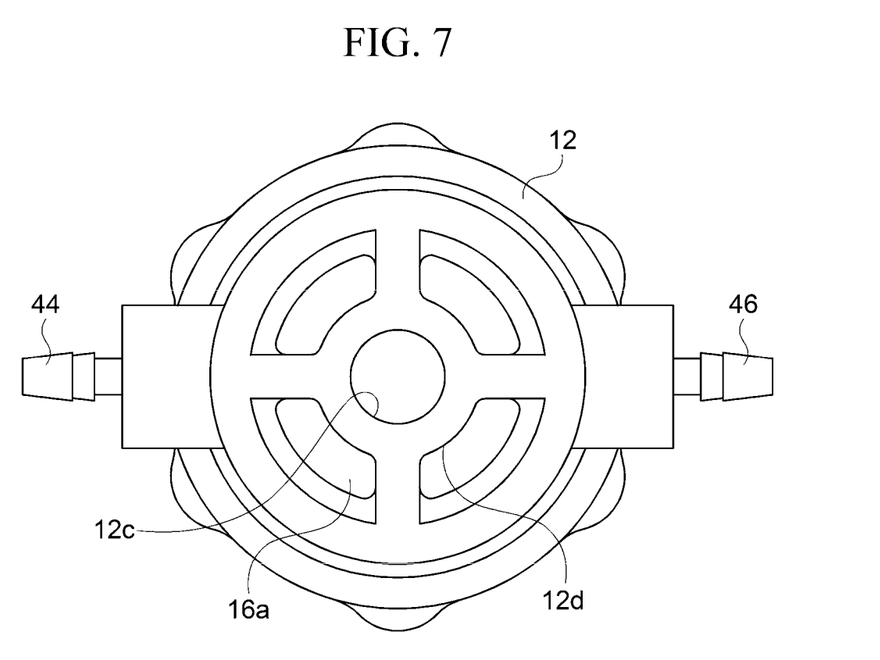
FIG. 7 is a bottom view illustrating a lower portion of the mounting unit of the bioenvironmental simulation device according to an embodiment of the present invention.

FIG. 4 is a perspective view of the mounting unit and the pressure sensor of the bioenvironmental simulation device according to an embodiment of the present invention, FIG. 5 is an exploded perspective view of the mounting unit and the pressure sensor of the bioenvironmental simulation device according to an embodiment of the present invention, FIG. 6 is a cross-sectional view illustrating the mounting unit of the bioenvironmental simulation device according to an embodiment of the present invention and flow of the culture liquid, and FIG. 7 is a bottom view illustrating a lower portion of the mounting unit of the bioenvironmental simulation device according to an embodiment of the present invention.

The mounting unit 10 may include the unit body 12 having an opening 12a formed at one side thereof, and a body cover 14 that opens and closes the opening 12a. The cells to be measured and a separation membrane 22 may be disposed inside the unit body 12, and a space through which the culture liquid can flow may be formed therein. As the body cover 14 is coupled to the unit body 12, an inner space 12b may be formed therein.

The unit body 12 and the body cover 14 may include first and second transmissive members 16a and 16b (see FIG. 6), respectively. The first and second transmissive members 16a and 16b may be configured so that air can penetrate but the culture liquid does not pass therethrough. The first and second transmissive members 16a and 16b may be provided in such a manner that inner surfaces thereof are communicated with the inner space 12b so that air passing through the first and second transmissive members 16a and 16b inflows into the inner space 12b. The first transmissive member 16a may be exposed to the outside through a through hole 12d (see FIG. 7) formed in the lower portion of the unit body 12, and the second transmissive member 16b may be exposed to the outside through an upper surface of the body cover 14. Due to this configuration, the cells to be measured may breathe through the air inflowing and outflowing through the transmissive members 16a and 16b, and the culture liquid therein may be prevented from leaking to the outside. The types of the transmissive members 16a and 16b are not limited. As an example, the transmissive members 16a and 16b may include polydimethylsiloxane (PDMS). In the present embodiment, the transmissive members 16a and 16b are illustrated as a member having a predetermined thickness, but it is not limited thereto. As an example, the transmissive members 16a and 16b may be formed of at least one membrane.

The mounting unit 10 may include the separation member 20. The separation member 20 is provided to divide the inner space 12b formed therein. The separation member 20 may be provided to divide the inner space 12b into a first space 32 and a second space 42 as shown in FIG. 6.

The mounting unit 10 may include a first mounting part 30 forming the first space 32 and a second mounting part 40 forming the second space 42. The first and second mounting parts 30 and 40 may be partitioned by the separation member 20. The second mounting part 40 may be disposed outside of the first mounting part 30 in the first direction W1. The first direction W1 may mean the resultant direction of the rotational force and gravity.

The separation member 20 may include the separation membrane 22. It may be configured so that one surface of the separation membrane 22 faces the first space 32 and the other surface of the separation membrane 22 faces the second space 42. That is, the first and second spaces 32 and 42 may be partitioned by the separation membrane 22.

The separation membrane 22 may include first and second cell placing surfaces 22a and 22b formed on one surface and the other surface thereof, on which the cells are placed. The cells may be placed on the first and second cell placing surfaces 22a and 22b of the separation membrane 22, respectively, so that an interaction can occur therebetween. That is, a first cell to be measured disposed on the first cell placing surface 22a and a second cell to be measured disposed on the second cell placing surface 22b may interact through the separation membrane. The cells disposed on the first and second cell placing surfaces 22a and 22b may be the same cell or different types of cells. The first and second cell placing surfaces 22a and 22b may be disposed to face the first space 32 and the second space 42, respectively. The first and second cell placing surfaces 22a and 22b may be one component of the first and second mounting parts 30 and 40, respectively. The first and second cells to be measured placed on the first and second cell placing surfaces 22a and 22b may be subjected to a shear force applied in a flow direction of the first and second culture liquids by the flow of the first and second culture liquids, respectively. The flow direction of the first and second culture liquids may be a second direction W2 perpendicular to the first direction W1.

The separation member 20 may include a separation membrane mounting member 24 formed along a circumference of the separation membrane 22 so that the separation membrane 22 can be mounted inside the unit body 12. The separation membrane mounting member 24 may have an inner side on which the separation membrane 22 is located, and an outer surface which can be mounted on an inner surface of the unit body 12.

The mounting unit 10 may include a first inlet 34, a first outlet 36, a second inlet 44, and a second outlet 46. The first inlet 34, the first outlet 36, the second inlet 44, and the second outlet 46 may be disposed in the second direction W2 perpendicular to the first direction W1. Due to this arrangement, the first and second culture liquids flowing through the first inlet 34, the first outlet 36, the second inlet 44, and the second outlet 46 may apply the shear force to the cells to be measured in the second direction. In addition, as the inlets and outlets are arranged in the second direction, it is possible to minimize cancelling-out of the pressure and shear force due to the rotational force.

The first inlet 34 and the first outlet 36 may be provided so that the first culture liquid inflows and outflows therethrough. The first inlet 34 and the first outlet 36 may form a first flow passage 66a passing through the first space 32 together with the first mounting part 30. Since the first inlet 34 and the first outlet 36 are arranged in the second direction W2, the first flow passage 66a may also be formed in the second direction W2. The first culture liquid stored in the first culture liquid storage part 62a may inflow into the first inlet 34 at a predetermined flow rate by the first supply part 64a. The first culture liquid inflowing into the first inlet 34 moves along the first flow passage 66a, applies a shear force to the first cell to be measured, and may be discharged through the first outlet 36.

The second inlet 44 and the second outlet 46 may be provided so that the second culture liquid inflows and outflows therethrough. The second inlet 44 and the second outlet 46 may form a second flow passage 66b passing through the second space 42 together with the second mounting part 40. Since the second inlet 44 and the second outlet 46 are arranged in the second direction W2, the second flow passage 66b may also be formed in the second direction W2. The second culture liquid stored in the second culture liquid storage part 62b may be introduced into the second inlet 44 at a predetermined flow rate by the second supply part (not illustrated). The second culture liquid inflowing into the second inlet 44 moves along the second flow passage 66b, applies a shear force to the second cell to be measured, and may be discharged through the second outlet 46.

The controller (not illustrated) may control a speed at which the rotational shaft is rotated by the rotational force application part 50, thus to adjust the pressure to be applied to the cells mounted in the mounting unit 10. In addition, the controller may independently control the flow rates of the first and second culture liquids discharged by the culture liquid flow device 60, thus to control the shear force applied to the cells to be measured by the first and second culture liquids passing through the first and second spaces 32 and 42.

More specifically, the controller may allow the pressure and shear force that satisfy an appropriate pressure condition and an appropriate shear force condition to be applied to the cells, based on the type of the cell, an appropriate pressure and the appropriate shear force condition which are matched with the type of the cell. That is, the controller may calculate a speed of rotational motion of the mounting unit 10 that satisfies the appropriate pressure condition to provide the calculated speed to the rotational force application part 50, and calculate a discharge speed of the first and second culture liquids that satisfy the appropriate shear force condition to provide the calculated discharge speed to the culture liquid flow device 60.

The controller may include a computing device such as a microprocessor. In order to operate the controller, the input unit 92 may receive necessary information such as a type of the cell from a user of the bioenvironmental simulation device 1. In addition, a database (not illustrated) may store information necessary for operating the bioenvironmental simulation device 1, such as the appropriate pressure condition and the appropriate shear force condition, which are matched and stored for each type of the cell, that is, determined for each type of the cell. In addition, the output unit 94 may provide the user with information necessary for operating the bioenvironmental simulation device 1 (e.g., information such as a rotational speed of the mounting unit 10, flow rate of the culture liquid and the like).

The input unit 92 and the output unit 94 may be provided to be exposed to the outside of a device body 5, and the controller and the database may be provided inside the device body 5, respectively. The input unit 92 may include a keypad, etc. for receiving more specific information (e.g., a preset blood pressure value, a blood flow rate, the appropriate pressure condition, and the appropriate shear force condition, etc. to be stored in the database) from the user. The output unit 94 may include a visual output device such as a display or an audible output device such as a speaker.

The database may be implemented through a computer readable recording medium, and examples of such a computer readable recording medium may include: magnetic media such as a hard disk, floppy disk, and magnetic tape; optical recording media such as a CD-ROM and DVD; magneto-optical media such as a floptical disk; and a hardware device such as a flash memory, which is specially configured to store and execute program instructions.

As described above, according to an embodiment of the present invention, it is possible to easily simulate an environment in which the pressure is applied to the cells by using the rotational force and shear force. Furthermore, in an embodiment of the present invention, various convenient functions may be provided to the user by using the appropriate pressure condition and the appropriate shear force condition which are determined for each type of the cell. Hereinafter, such functions will be described.

The appropriate pressure and shear force conditions stored in the database may be determined to include various information. For example, the appropriate pressure and appropriate shear force conditions may be determined based on a pressure and a shear force within a range in which cells to be tested can survive for a predetermined critical time in a predetermined critical probability or higher. The reason is that the appropriate pressure and shear force conditions that ensure a certain level or more of survival rate may be different for each cell. The controller may control the device so that the pressure and shear force input through the input unit 92 within a range matched with the type of the cells to be tested are applied to the cells to be tested, based on the appropriate pressure and appropriate shear force conditions.

In addition, according to an embodiment of the present invention, when the input unit 92 receives the blood pressure and blood flow rate set values from the user, the controller may calculate values of actual pressure and shear force, which are the pressure and shear force applied to the cells to be tested under conditions in which the cells to be tested exist in a body having a blood pressure and a blood flow rate as much as the blood pressure and blood flow rate set values, and control the rotational force application part 50 and the culture liquid flow device 60 so that the pressure and shear force as much as the values of the actual pressure and shear force are applied to the cells to be tested. That is, if the user only inputs the type of the cell to be tested and the blood pressure and blood flow rate of the body to be simulated through the input unit 92, the controller will automatically determine the rotational speed of the mounting unit 10 and the flow rate of the culture liquid based on the input information.

Hereinafter, a bioenvironmental simulation method by the bioenvironmental simulation device of the present invention will be described.

First, cells to be measured are mounted on the first and second cell placing surfaces 22a and 22b of the separation membrane 22, and the mounting unit 10 is mounted on the unit mount 70.

Then, based on a rotation radius of the mounting unit 10, the type of the cell to be measured, and the appropriate pressure condition and the appropriate shear force condition matched with the type of the cell to be measured, the controller may calculate a speed of rotational motion for allowing the pressure that satisfies the appropriate pressure condition to be applied to the cell, and calculate a flow rate so that the flow rate that satisfies the appropriate shear force condition is applied to the cell.

Finally, the controller may control the mounting unit 10 to rotate at the calculated speed of rotational motion and circulate the culture liquid at the calculated flow rate.

In detail, the rotational force application part 50 may transmit the rotational force thereof to the first and second cell placing surfaces 22a and 22b of the mounting unit 10. The first and second cell placing surfaces 22a and 22b of the mounting unit 10 may be rotated at a preset rotational speed. The mounting unit 10 may perform a circular motion by the rotational force application part 50, thus to apply a pressure due to the rotational force to the first and second cell placing surfaces 22a and 22b.

In addition, the first and second culture liquids may pass through the first and second flow passages 66a and 66b, in which the first and second cell placing surfaces 22a and 22b are located, at a preset flow rate. Thereby, it is possible to apply the shear force to the cells to be measured placed on the first and second cell placing surfaces 22a and 22b.

Any one of the pressure due to the rotational force and the shear force due to the first and second culture liquids may be first applied to the cells to be measured, or both of them may be applied at the same time.

Hereinafter, a bioenvironmental simulation device according to another embodiment of the present invention will be described. In the following description, configurations identical to the above-described configurations will not be described to avoid duplication.

Figure 8:
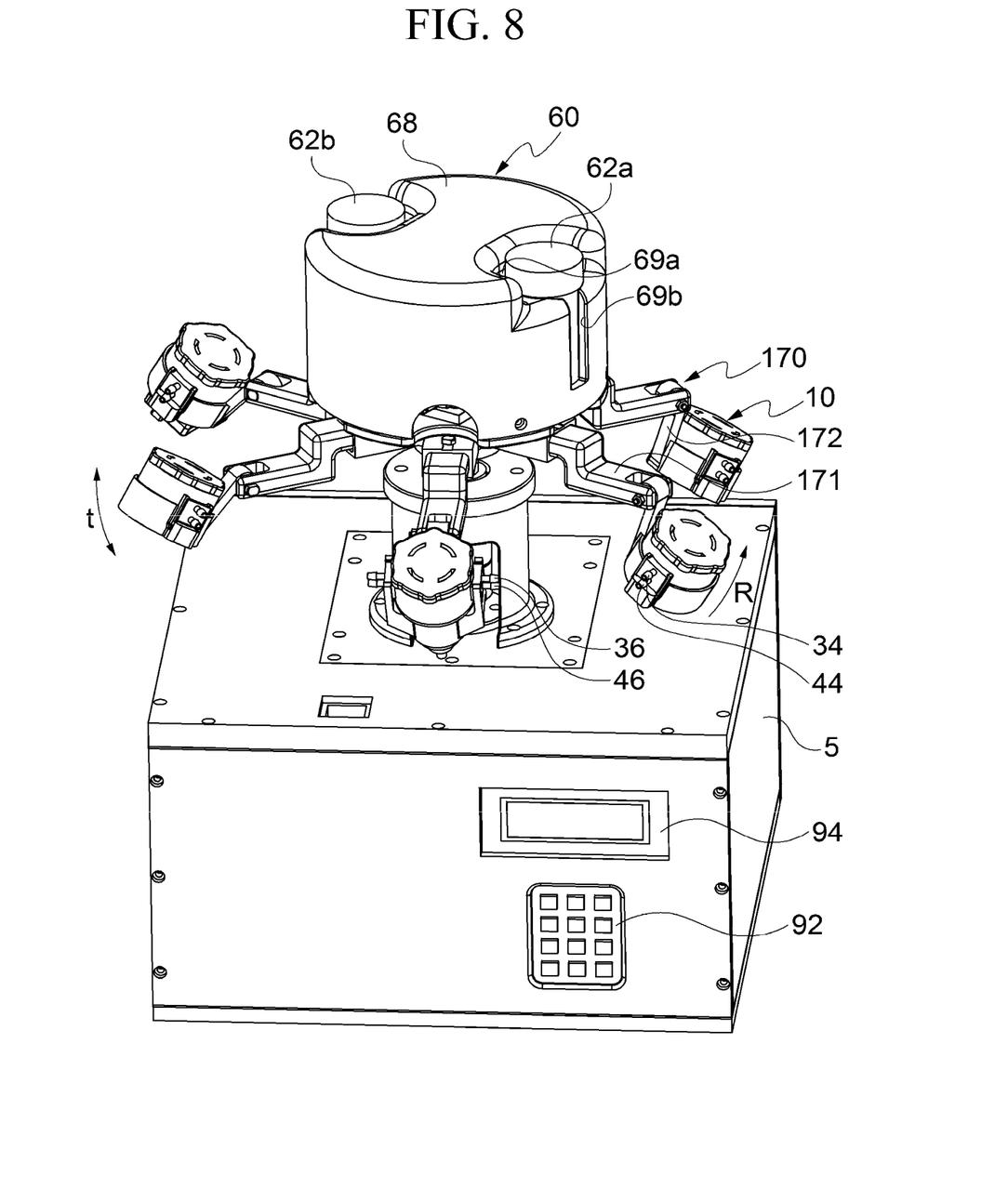
FIG. 8 is a perspective view of a bioenvironmental simulation device according to another embodiment of the present invention.

A unit mount 170 may include a plurality of divided leg supports 171 and a plurality of divided mount legs 172 which are rotatably provided on the leg supports 171.

The plurality of leg supports 171 are provided to be connected to with the rotational force application part 50, and to rotate about a rotation axis when a rotational force is generated by the rotational force application part 50.

Each of the plurality of mount legs 172 may be rotatably coupled to the plurality of leg supports 171. The plurality of mount legs 172 may be configured to be radially disposed from the rotational force application part 50. Each of the mounting units 10 may be mounted on the plurality of mount legs 172 radially disposed with respect to the rotational force application part 50.

The plurality of mount legs 172 may be configured in such a way that a direction formed by the resultant force with the gravity is changed according to a magnitude of the rotational force applied from the rotational force application part 50, and thereby, when the rotational force is increased, they are widened together with the mounting units 10 so that an angle formed by the same with the ground is decreased. Due to this configuration, it is possible to apply the pressure in a direction perpendicular to the first and second cell placing surfaces 22a and 22b on which the cells disposed in the mounting units 10 are placed. The plurality of mount legs 172 may vertically operate the mounting units 10 in a direction shown by an arrow t in FIG. according to the magnitude of the rotational force generated by the rotational force application part 50.

In detail, when the rotational force applied from the rotational force application part 50 is greater than a predetermined speed, the plurality of unit mounts 70 and the plurality of mounting units 10 are gradually widened in parallel to the ground. That is, the mount legs 172 and the mounting units 10 mounted on the mount legs 172 may be located at a higher portion than when the rotational force is at a level of the predetermined speed.

Conversely, when the rotational force applied from the rotational force application part 50 is less than the predetermined speed, the plurality of unit mounts 70 and the plurality of mounting units 10 are gradually narrowed in a direction perpendicular to the ground. That is, the mount legs 172 and the mounting units 10 mounted on the mount legs 172 may be located at a lower portion than when the rotational force is at the level of the predetermined speed.

In the present embodiment, the configuration, in which the mount legs 172 are rotatably coupled to the leg supports 171, and the leg supports 171 are connected to the rotational force application part 50, has been described. However, it is not limited thereto, and the mount legs 172 may be directly coupled to the rotational force application part 50 in a rotatable manner. That is, any configuration may be used so long as it can sufficiently change the angle formed by the mounting units 10 with the ground by the mount legs 172 according to the magnitude of the rotational force generated by the rotational force application part 50.

Further, a separate circulation tube is not illustrated in FIG. 8, but similar to the above-described circulation tube in FIGS. 1 to 3, the plurality of mounting units 10 may be connected to each other or may be connected to the culture liquid flow device 60 by the circulation tubes.

As such, specific embodiments of the present invention have been illustrated and described in detail. However, the present invention is not limited to the above embodiments, and it will be understood by those skilled in the art that various alterations and modifications may be implemented without departing from technical spirits of the invention described in the following claims.

What is claimed is:

1. A bioenvironmental simulation device, comprising:
a mounting unit on which cells to be measured are placed;
a motor configured to rotate the mounting unit so as to apply a rotational force to the cells to be measured placed on the mounting unit; and
a culture liquid flow device through which a culture liquid flows across the mounting unit, wherein the culture liquid flows by the culture liquid flow device so as to apply a shear force to the cells to be measured,
wherein the mounting unit comprises:
a unit body forming an inner space;
a separation membrane disposed in the unit body and partitioning the inner space into a first space and a second space disposed under the first space;
a first mounting part including the first space through which a first culture liquid passes; and
a second mounting part including the second space through which a second culture liquid passes,
wherein the cells are placed on one surface and an opposing surface of the separation membrane,
wherein the rotational force and the shear force are applied to the one surface and the opposing surface of the separation membrane.

2. The bioenvironmental simulation device according to claim 1,
wherein the first mounting part has a first cell placing surface on which a first cell to be measured is placed on the one surface of the separation membrane,
wherein the first space faces the first cell placing surface;
wherein the second mounting part has a second cell placing surface on which a second cell to be measured interacting with the first cell to be measured is placed on the opposing surface of the separation membrane,
wherein the second space faces the second cell placing surface.

3. The bioenvironmental simulation device according to claim 2, wherein the first and second culture liquids are configured to pass through the first and second spaces at independent flow rates.

4. The bioenvironmental simulation device according to claim 3, wherein the culture liquid flow device comprises:
a first supply part configured to circulate the first culture liquid passing through the first space; and
a second supply part configured to circulate the second culture liquid passing through the second space, wherein the second supply part is operated independently from the first supply part.

5. The bioenvironmental simulation device according to claim 2, wherein the first and second cell placing surfaces, on which the first and second cells to be measured are respectively disposed, are subjected to:
a pressure applied due to a resultant force of gravity and a rotational force generated by the motor in a first direction; and
a shear force applied due to a flow of the first and second culture liquids by the culture liquid flow device in a second direction perpendicular to the first direction.

6. The bioenvironmental simulation device according to claim 5, wherein the second mounting part is disposed outside of the first mounting part in the first direction.

7. The bioenvironmental simulation device according to claim 5, wherein the at least one mounting unit comprises:
a first inlet and a first outlet which are connected to the first mounting part and configured to allow the first culture liquid to inflow and outflow through the first space; and
a second inlet and a second outlet which are connected to the second mounting part and configured to allow the second culture liquid to inflow and outflow through the second space,
wherein the first inlet, the first outlet, the second inlet, and the second outlet are arranged in the second direction with respect to the first and second mounting parts, respectively.

8. The bioenvironmental simulation device according to claim 5, further comprising a pressure sensor disposed outside of the at least one mounting unit in the first direction to detect a pressure in the mounting unit.

9. The bioenvironmental simulation device according to claim 2, wherein the first and second mounting parts comprise a transmissive member, of which one side faces the first and second spaces, and the other side is a transmissive surface exposed to an outside, which allows air to penetrate into the first and second spaces.

10. The bioenvironmental simulation device according to claim 9, wherein the transmissive member comprises polydimethylsiloxane (PDMS).

11. The bioenvironmental simulation device according to claim 2, wherein the at least one mounting unit comprises a plurality of mounting units radially disposed about the motor; and
the bioenvironmental simulation device further comprises a unit mount configured to transmit a rotational force of the motor to the plurality of mounting units, and rotate together with the plurality of mounting units.

12. The bioenvironmental simulation device according to claim 11, wherein the unit mount comprises:
a plurality of mount legs which are radially divided and disposed, and the plurality of mounting units are respectively mounted thereon, such that an angle formed between the mount legs and a ground is changed according to the rotational force of the motor.

13. The bioenvironmental simulation device according to claim 1, further comprising:
an input unit configured to input a type of the cell to be measured;
a database configured to store an appropriate rotational force and an appropriate shear force condition which are matched with the type of the cell to be measured; and
a controller configured to control the motor and the culture liquid flow device so that a pressure and a shear force satisfying an appropriate pressure condition and the appropriate shear force condition are applied to the cells to be measured, based on the type of the cell to be measured, the appropriate pressure condition and the appropriate shear force condition which are matched with the type of the cell to be measured.

14. The bioenvironmental simulation device according to claim 13, wherein the appropriate pressure condition comprises information on a relationship between a blood pressure of a body and the pressure applied to the cells to be measured under a condition in which the cells to be measured exist in the body; and
the controller calculates a value of an actual pressure which is the pressure applied to the cells to be measured under a condition in which the cells to be measured exist in the body having a blood pressure as much as a preset blood pressure value using the information in the appropriate pressure condition, and controls the motor so that a pressure as much as the calculated value of the actual pressure is applied to the cells to be measured.

15. The bioenvironmental simulation device according to claim 13, wherein the appropriate shear force condition comprises information on a relationship between a blood flow rate of a body and the shear force applied to the cells to be measured under a condition in which the cells to be measured exist in the body; and the controller calculates a value of an actual shear force which is a shear force applied to the cells to be measured, under a condition in which the cells to be measured exist in the body having a blood flow rate as much as a predetermined blood flow rate using the information in the appropriate shear force condition, and controls the culture liquid flow device so that a shear force as much as the calculated value of the actual shear force is applied to the cells to be measured.

16. The bioenvironmental simulation device according to claim 13, wherein the controller calculates a speed of rotational motion of the mounting unit, which satisfies the appropriate pressure condition, to provide the calculated speed to the motor, and calculates a flow rate of the culture liquid, which satisfies the appropriate shear force condition, to provide the calculated flow rate to the culture liquid flow device.

17. The bioenvironmental simulation device according to claim 13, wherein the appropriate pressure condition and the appropriate shear force condition are determined based on the pressure and the shear force within a range in which the cells to be measured can survive for a predetermined critical time in a predetermined critical probability or higher.

* * * * *